United States Patent [19]

Merrill et al.

[11] Patent Number: 5,529,787
[45] Date of Patent: Jun. 25, 1996

[54] HYDROMORPHONE THERAPY

[75] Inventors: Sonya Merrill, San Jose; Atul D. Ayer, Palo Alto; Navjot Chadha, Sunnyvale; Anthony L. Kuczynski, Mt. View, all of Calif.

[73] Assignee: Alza Corporation, Palo Alto, Calif.

[21] Appl. No.: 271,593

[22] Filed: Jul. 7, 1994

[51] Int. Cl.⁶ .............. A61K 9/20; A61K 9/22; A01N 43/08

[52] U.S. Cl. .......... 424/465; 424/468; 424/470; 424/472; 424/475; 514/468

[58] Field of Search ............... 424/465, 468, 424/470, 472, 475; 514/468

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,201 | 9/1978 | Theeuwes et al. | 128/260 |
| 4,111,202 | 9/1978 | Theeuwes | 128/260 |
| 4,327,725 | 5/1982 | Cortese et al. | 128/260 |
| 4,464,378 | 8/1984 | Hussain | 424/260 |
| 4,576,604 | 3/1986 | Guittard et al. | 604/890 |
| 4,612,008 | 9/1986 | Wong et al. | 604/892 |
| 4,844,907 | 7/1989 | Elger et al. | 424/465 |
| 5,021,053 | 6/1991 | Barclay et al. | 604/892 |
| 5,198,229 | 3/1993 | Wong et al. | 424/473 |
| 5,326,571 | 7/1994 | Wright et al. | 424/473 |

*Primary Examiner*—José G. Dees
*Assistant Examiner*—Rosalynd A. Williams
*Attorney, Agent, or Firm*—Paul L. Sabatine; Felissa H. Cagan; Richard T. Ito

[57] ABSTRACT

A hydromorphone composition, a hydromorphone dosage form and a method for administering hydromorphone are disclosed, indicated for the management of pain.

4 Claims, No Drawings

HYDROMORPHONE THERAPY

FIELD OF THE INVENTION

This invention pertains to a novel therapeutic composition comprising hydromorphone. The invention concerns also a novel dosage form comprising hydromorphone. Additionally, the invention relates to a method of administering a dose amount of hydromorphone, and to a method of administering a dosage form for delivering hydromorphone to produce analgesic therapy.

BACKGROUND OF THE INVENTION

Hydromorphone is an analgesic with its principal therapeutic effect the relief of pain. The precise mechanism of action of hydromorphone is not known, although it is thought to relate to the existence of hydromorphone receptors in the central nervous system. Generally, the analgesic action of parenterally administered hydromorphone is apparent within fifteen minutes and the onset of action of oral hydromorphone is somewhat slower, with analgesia occurring within thirty minutes. In human plasma, the half-life of hydromorphone is about two and one-half hours. Hydromorphone is indicated for the relief of moderate to severe pain, such as that due to surgery, cancer, trauma, biliary colic, renal colic, myocardial infarction and burns. A pharmaceutically acceptable dosage form for oral administering hydromorphone to provide analgesic therapy beyond its short half-life at a controlled rate over an extended period of time appears to be lacking in the pharmaceutical and medical arts. The pharmacological properties of hydromorphone are known in *Pharmaceutical Sciences,* Remington, 17th Ed, pp. 1099-1044 (1985); and in the *Pharmacological Basis of Therapeutics,* Goodman and Rail, 8th Ed, pp 485–518 (1990).

SUMMARY OF THE INVENTION

In view of the foregoing presentation, it is immediately apparent that a serious need exists for an improvement in the delivery of hydromorphone for its therapeutic analgesic effect. The need exists to provide a novel therapeutic composition comprising hydromorphone, the need exists to provide a novel dosage form comprising hydromorphone, and the need to provide a novel method of administering hydromorphone to a patient in need of hydromorphone therapy. The invention provides an oral, relatively easy mode and manner of hydromorphone administration in comparison with intramuscular, subcutaneous, and intravenous routes of administration.

DESCRIPTION OF THE INVENTION

The drug, hydromorphone, as embraced by this invention comprises 4,5-epoxy-3-hydroxy-17-methylmorphinan-6-one possessing analgesic therapy. The hydromorphone is known in the *Merck Index,* 11 ed, p 762 (1990). Representative of hydromorphones for this invention comprise a member selected from the group consisting of hydromorphone, its pharmaceutically acceptable salt, hydromorphone sulfate, hydromorphone hydrochloride, hydromorphone trifluoracetate, hydromorphone thiosemicarbazone hydrochloride, hydromorphone pentafluoropropionate, hydromorphone p-nitrophenylhydrozone, s hydromorphone o-methyloxine, hydromorphone thiosemicarbazone, hydromorphone semicarbazone, hydropmorphone phenylhydroazone, hydromorphone hydrazone, hydromorphone hydrobromide, hydromorphone mucate, hydromorphone methylbromide, hydromorphone oleate, hydromorphone n-oxide, hydromorphone acetate, hydromorphone phosphate dibasic, hydromorphone phosphate monobasic, hydromorphone inorganic salt, hydromorphone organic salt, hydromorphone acetate trihydrate, hydromorphone bis(heptafluorobutyrate), hydromorphone bis(methylcarbamate), hydromorphone (bis(pentafluoropropianate), hydromorphone bis(pyridine-3-carboxylate), hydromorphone bis(trifluoroaceatate), hydromorphone bitartrate, hydromorphone chlorhydrate, and hydromorphone sulfate pentahydrate.

The following examples are merely illustrative of the invention and they should not be considered as limiting the scope of the invention in any way as these examples and other equivalents thereof will become apparent to those versed in the art.

Example 1

A novel, therapeutic composition comprising hydromorphone, wherein the hydromorphone is a member selected from the group consisting of hydromorphone pharmaceutically acceptable base and hydromorphone pharmaceutically acceptable salt is prepared as follows: first, 175 g of hydromorphone hydrochloride, 647.5 g of poly(ethylene oxide) possessing a 200,000 molecular weight, and 43.75 g of poly(vinylpyrrolidone) having an average molecular weight of 40,000 are added to a Hobart® planetary mixing bowl and the ingredients dry mixed for 10 minutes. Then, 331 g of denatured, anhydrous alcohol is slowly added to the blended ingredients with continuous blending for approximately 10 minutes. Next, the freshly prepared wet granulation is passed through a 20 mesh screen, allowed to dry at 25° C. for about 20 hours and then passed through a 16 mesh screen. Next, the granulation is transferred to a Hobart® planetary mixture and lubricated with 8.75 g of magnesium stearate, to produce a therapeutic hydromorphone composition. The composition is compressed into tablets comprising 35 mg of hydromorphone hydrochloride. The tablets are compressed under 8.5 tons of pressure to provide sustained-release hydromorphone hydrochloride tablets.

Example 2

The therapeutic compositions manfuctured by following the above example provides compositions comprising 1 mg to 1000 mg of a member selected from the group consisting of hydromorphone, hydromorphone base, hydromorphone salt, and hydromorphone derivative; at least one polymeric carrier for the hydromorphone selected from 25 mg to 500 mg of poly(alkylene oxide) comprising a 150,000 to 500,000 molecular weight represented by poly(methylene oxide), poly(ethylene oxide), poly(propylene oxide), poly(isopropylene oxide) and poly(butylene oxide) or a polymeric carrier for the hydromorphone consisting of 25 mg to 500 mg of a carboxymethylcellulose having a 10,000 to 300,000 molecular weight represented by a member selected from the group consisting of alkali carboxymethylcellulose, sodium carboxymethylcellulose and potassium carboxymethylcellulose; 1 mg to 50 mg of a poly(vinyl) polymer possessing a 10,000 to 300,000 molecular weight as represented by poly(vinyl pyrrolidone), copolymer of poly(vinyl pyrrolidone and vinyl acetate), copolymer of poly(vinyl pyrrolidone and vinyl alcohol), copolymer of poly(vinyl pyrrolidone and vinyl chloride), copolymer of poly(vinyl pyrrolidone and vinyl fluoride), copolymer of poly(vinylpyrrolidone and vinyl butyrate), copolymer of poly(vinyl pyrrolidone and vinyl laurate) and copolymer of poly(vinylpyrrolidone with vinyl stearate); and 0 to 7.5 mg of a lubricant represented by a member selected from the group consisting of magnesium stearate, calcium stearate, potassium oleate, sodium stearate, stearic acid and sodium palmitate. The therapeutic composition may contain other ingredients, for example, colorants, compression aids, and binders. The composition can be compressed at ⅛ to 10 ton-force, to yield an orally administrable tablet comprising hydromorphone.

Example 3

The therapeutic composition provided by the invention, can be dry compressed into an orally administrable dosage form. For example, a mixture of dry-powder ingredients comprising hydromorphone pharmaceutically acceptable base, or hydromorphone pharmaceutically acceptable salt as represented by hydrochloride, hydrobromide, sulfate, bisulfate, acetate, valerate, oxalate, oleate, laurate, borate, benzoate, lactate, phosphate, tosylate, citrate, maleate, fumarate, succinate, tartrate, and napsylate; a tablet excipient represented by 0 to 200 mg (milligrams) of microcrystalline cellulose, 25 to 500 mg of sodium carboxymethylcellulose of 10,000 to 300,000 molecular weight; 1 to 50 mg of a binder agent represented by poly(vinylpyrrolidone) of 10,000 to 300,000 molecular weight, hydropropymethylcellulose of 9,200 to 75,000 molecular weight, and gelatin; and 0 to 7.5 mg of a lubricant such as stearic acid, calcium stearate, and magnesium stearate; are dried sieved and mixed with other optional ingredients such as a surfactant and flavoring agent, mixed, and fed to a tablet press and compressed to yield dry-compressed hydromorphone tablets for oral administration to a patient in need of hydromorphone analgesic pain relief. In a manufacture provided by the invention, a therapeutic composition made by wet granulation or dry granulation processes can be surrounded with a semipermeable polymeric wall. The semipermeable wall is pervious to fluid, impervious to hydromorphone, and an exit means, such as a passageway through the semipermeable ,wall, provides for the delivery of hydromorphone at a controlled-sustained rate through the exit means over time.

Example 4

A dosage form adapted, designed and shaped as an osmotic drug delivery device is manufactured as follows: first, 175 g of hydromorphone hydrochloride, 647.5 g of poly(ethylene oxide) possessing a 200,000 molecular weight, and 43.75 g of poly(vinylpyrrolidone) having a 40,000 molecular weight are added to a mixer and mixed for 10 minutes. Then, 331 g of denatured anhydrous alcohol is added to the blended materials with continuous mixing for 10 minutes. Then, the wet granulation is passed through a 20 mesh screen, allowed to dry at room temperature for 20 hours, and then passed through a 16 mesh screen. Next, the granulation is transferred to the mixer, mixed and lubricated with 8.75 g of magnesium stearate.

Then, a displacement or push composition for pushing the therapeutic, hydromorphone composition from the dosage form is prepared as follows: first 3910 g of hydroxypropylmethylcellulose possessing a 11,200 molecular weight is dissolved in 45,339 of water. Then, 101 g of butylated hydroxytoluene is dissolved in 650 g of denatured anhydrous alcohol. Next, 2.5 kg of the hydroxypropylmethylcellulose aqueous solution is added with continuous mixing to the butylated hydroxytoluene alcohol solution. Then, binder solution preparation is completed by adding with continuous mixing the remaining hydroxypropylmethylcellulose aqueous solution to the butylated hydroxytoluene alcohol solution.

Next, 36,000 g of sodium chloride is sized using a Quadro Comil® mill equipped with a 21 mesh screen. Then, 1200 g of ferric oxide is passed through a 40 mesh screen. Then, the screened materials, 76,400 g of pharmaceutically acceptable poly(ethylene oxide) possessing a 7,500,000 molecular weight, 2500 g of hydroxypropylmethylcellulose having a 11,200 molecular weight are added to a Glatt® Fluid Bed Granulation's bowl. The bowl is attached to the granulator and the granulation process is initiated for effecting granulation. Next, the dry powders are air suspended and mixed for 10 minutes. Then, the binder solution is sprayed from 3 nozzles onto the powder. The granulating is monitored during the process as follows: total solution spray rate of 800 g/min; inlet temperature 43° C. and air flow 4300 m³/hr. At the end of solution spraying, 45,033 g, the coated granulated particles is followed by a drying process for 35 minutes. The coated granules are sized using a Quadro Comil® mill with a 8 mesh screen. The granulation is transferred to a Tote® Tumbler, mixed and lubricated with 281,7 g of magnesium stearate.

Next, the drug composition comprising the hydromorphone hydrochloride and the push composition are compressed into bilayer tablets on a Kilian® Tablet press. First, 176 mg of the hydromorphone hydrochloride composition is added to the die cavity and precompressed, then, 135 mg of the push composition is added and the layers are pressed under a pressure head of 3 metric tons into a ¹¹⁄₃₂ inch (0.873 cm) diameter contacting layer arrangement.

The bilayered arrangements are coated with a semipermeable wall. The wall forming composition comprises 100% cellulose acetate having a 39.8% acetyl content. The wall-forming composition is dissolved in acetone:water (95:5 wt:wt) cosolvent to make a 4% solid solution. The wall-forming composition is sprayed onto and around the bilayers in a 24 inch (60 cm) Vector® Hi-Coater.

Next, one 20 mil (0.508 mm) exit passageway is drilled through the semipermeable wall to connect the drug hydromorphone layer with the exterior of the dosage form. The residual solvent is removed by drying for 72 hours at 45° C. and 45% humidity. Next, the osmotic dosage systems are dried for 4 hours at 45° C. to remove excess moisture. The dosage forms produced by this manufacture comprises 35.20 mg of hydromorphone, 130.24 mg of poly(ethylene oxide) of 200,000 molecular weight, 8.80 mg of poly(vinylpyrrolidone) of 40,000 molecular weight, and 1.76 mg of magnesium stearate. The push composition comprises 85.96 mg of poly(ethylene oxide) of 7,500,000 molecular weight, 40.50 mg of sodium chloride, 6.75 mg of hydroxypropylmethylcellulose, 1.35 mg of red ferric oxide, 0.34 mg of magnesium stearate, and 0.10 mg of butylated hydroxytoluene. The semipermeable wall comprises 38.6 mg of cellulose acetate comprising a 39.8% acetyl content. The dosage form comprises one passageway, 20 mil (0.508 mm) and the dosage form had a hydromorphone hydrochloride mean release rate of 1.6 mg/hr over an extended period of 28 hours.

Example 5

The procedure of Example 4 is followed with all manufacturing procedures as described except in this example, the hydroxypropylmethyl-cellulose is replaced by a hydroxypropylmethylcellulose having a 300,000 molecular weight.

Example 6

The procedure of Example 4 is followed with all manufacturing procedures as described except in this example the poly(ethylene oxide) in the hydromorphone drug composition is replaced by sodium carboxymethyl-cellulose possessing a 250,000 molecular weight, and the poly(ethylene oxide) in the push composition is replaced by a sodium carboxymethyl-cellulose possessing a 700,000 molecular weight. In an inventive embodiment, the alkali carboxymethylcellulose present in the push composition possesses a greater molecular weight than the alkali carboxymethylcellulose of the hydromorphone drug composition.

Example 7

The dosage form prepared by the above examples can be manufactured with a semipermeable wall composition comprising 65 wt % to 100 wt % of a cellulose polymer comprising a member selected from the group consisting of a cellulose ester, cellulose diester, cellulose triester, cellulose ether, cellulose ester-ether, cellulose acylate, cellulose diacylate, cellulose triacetate, cellulose acetate butyrate and the like. The wall can comprise also from 0 wt % to 40 wt % of a cellulose ether selected from the group consisting of hydroxypropylecellulose, hydroxypropylmethylcellulose, hydroxypropylethylcellulose, hydroxypropylbutylcellulose, and hydroxypropyl-pentylcellulose. The wall can comprise further 0 wt % to 20 wt % of a polyethylene glycol. The total amount of all components comprising the wall is equal to 100 wt %. Semipermeable polymers useful for manufacturing the wall of the dosage form are disclosed in U.S. Pat. Nos. 3,845,000; 3,916,899; 4,008,719; 4,036,228; and 4,111,201. These patents are assigned to the ALZA Corporation of Palo Alto, Calif., the assignee of this patent application.

The wall, in another manufacture, can be prepared according to the above examples comprising the selectively permeable cellulose ether, ethyl cellulose. The ethyl cellulose comprises an ethoxy group with a degree of substitution, DS, of about 1.4 to 3, equivalent to 40% to 50% ethoxy content, and a viscosity range of 7 to 100 centipoise or higher. A representative wall comprises 45 wt % to 80 wt % ethylcellulose, from 5 wt % to 30 wt % hydroxypropylcellulose, and from 5 wt % to 30 wt % polyethylene glycol, with the total weight percent of all components comprising the wall equal to 100 wt %. In another manufacture the wall comprises 45 wt % to 80 wy % ethylcellulose, 5 wt % to 30 wt % hydroxypropylcellulose, and 2 wt % to 20 wt % of poly(vinylpyrrolidone). The total amount of all components comprising the wall is equal to 100 wt %. The ethylcellulose polymer is known in U.S. Pat. No. 4,519,801 assigned to the ALZA Corporation of Palo Alto, Calif.

Example 8

The dosage form, provided by the invention, comprises a hydromorphone drug composition consisting of 1 to 1000 mg of hydromorphone, hydromorphone base, hydromorphone salt, or hydromorphone derivative; at least one of 25 to 500 mg poly(alkylene oxide) of 150,000 to 500,000 molecular weight or 25 to 500 mg of a carboxymethylcellulose of 10,000 to 300,000 molecular weight; at least one of 1 to 50 mg of poly vinylpyrrolidone) of 10,000 to 300,000 molecular weight or 1 to 50 mg of hydroxypropylcellulose or hydroxypropylalkylcellulose of 7,500 to 75,000 molecular weight; and 0 to 10 mg of a lubricant such as magnesium stearate.

The dosage form, provided by the invention, comprises a push composition consisting of at least one of 15 to 250 mg of a poly(alkylene oxide) of 3,000,000 to 7,500,000 molecular weight, or 15 to 750 mg of a carboxymethylcellulose such as sodium carboxymethylcellulose, and potassium carboxymethylcellulose of 450,000 to 2,500,000 molecular weight; 0 to 75 mg of an osmagent, also known as osmotically solute represented by magnesium sulfate, sodium chloride, lithium chloride, potassium sulfate, sodium sulfate, lithium sulfate, potassium acid phosphate, mannitol, urea, inositol, magnesium succinate, tartaric acid, carbohydrates like raffinose, sucrose, glucose, lactose, fructose, sodium chloride and fructose, potassium chloride and dextrose; 1 to 50 mg of a hydroxyalkylcellulose selected from the group consisting of hydroxyethylcellulose, hydroxypropylcellulose, hydroxyisopropylcellulose, hydroxybutylcellulose, hydroxypropylmethyl-ellulose, hydroxypropylethylcellulose, hydroxypropylbuitylcellulose which hydroxyalkylcellulose comprises a 7,500 to 75,000 molecular weight; 0 to 10 mg of an antioxidant represented by d-alpha tocopherol acetate, dl-alpha tocopherol, ascorbyl palmitate, butylated hydroxyanidole, butylated hydroxytoluene and propyl gallate; 0 to 10 mg of a lubricant represented by magnesium stearate, calcium stearate, corn starch, potato starch, bentonite, citrus pulp, and stearic acid; and 0 to 10 mg of a colorant.

The expression, "exit means," as used for the dosage form of this invention, comprises means and methods suitable for the metered release of beneficial drug hydromorphone from the dosage form. The exit means comprises at least one passageway, orifice, through the wall for communicating with hydromorphone in the dosage form. The expression, "at least one passageway," comprises aperture, orifice, bore, pore, porous element through which the hydromorphone can migrate, hollow fiber, capillary tube, porous overlay, porous insert, and the like. The expression also includes a material that erodes or is leached from the wall in the fluid environment of use to produce at least one passageway in the dosage form. Representative materials suitable for forming at least one passageway, or a multiplicity of passageways, include an erodible poly(ortho ester), poly(ortho carbonate), poly(glycolic) acid, or poly(lactic) acid member in the wall, a gelatinous filament, poly(vinyl alcohol), leachable materials such as fluid removable pore forming polysaccharides, salts, oxides, or the like. A passageway or a plurality of passageways can be formed by leaching a material such as sorbitol, lactose, fructose and the like from the wall. The passageway can have any shape such as round, triangular, square, elliptical, and the like, for assisting in the metered release of morphine from the dosage form. The dosage form can be constructed with one or more passageways in spaced apart relations, or more than one passageway on a single surface of a dosage form. Passageways and equipment for forming passageways are disclosed in U.S. Pat. Nos. 3,845,770; 3,916,899; 4,063,064 and 4,088,864. Passageways of govern size formed by leaching are disclosed in U.S. Pat. Nos. 4,200,098 and 4,285,987.

Exemplary solvents used for the present purpose comprise inorganic and organic solvents that do not adversely harm hydromorphone and other materials and the final wall or the final compositions in the dosage form. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone, alcohol, methanol, ethanol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclo-hexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DISCLOSURE FOR USING THE INVENTION

The invention concerns also a method for administering 1 to 1000 mg of a hydromorphone to a patient in need of relief of pain. The method, in one administration comprises admitting orally into the patient 1 to 1000 mg of a hydromorphone selected from the group consisting of hydromorphone, or a hydromorphone salt that is administered from a therapeutic composition comprising 1 to 1000 mg of the hydromorphone, 25 to 500 mg of poly(alkylene oxide) having a 150,000 to 500,000 molecular weight, 1 to 50 mg of poly(vinylpyrrolidone) having a 40,000 molecular weight, and 0 to 7.5 mg of a lubricant, which composition provides hydromorphone therapy over an extended period of time.

The invention concerns also a method for administering 1 to 1000 mg of a hydromorphone by admitting orally I to 1000 mg of hydromorphone to a patient administered from a dosage form comprising a semipermeable wall permeable to aqueous-biological fluid and impervious to the passageway of hydromorphone, which semipermeable wall surrounds an internal space comprising a hydromorphone drug composition and a push composition, said hydromorphone drug composition comprising 1 to 1000 mg of hydromorphone, 25 to 500 mg of a poly(alkylene oxide) having a 150,000 to 500,000 molecular weight, 1 to 50 mg of a poly(vinylpyrrolidone) having a 40,000 molecular weight, and 0 to 7.5 mg of a lubricant, said push composition comprising 15 to 250 mg of a poly(alkylene oxide) of 3,000,000 to 7,500,000 molecular weight, 0 to 75 mg of an osmagent, 1 to 50 mg of a hydroxyalkylcellulose 0 to 10 mg of ferric oxide, 0 to 10 mg of a lubricant, and 0 to 10 mg of antioxidant; and exit means in the semipermeable wall for delivering the hydromorphone from the dosage form, by imbibing fluid through the semipermeable wall into the dosage form causing the hydromorphone composition to become dispensable and the push composition to expand and push the hydromorphone composition through the exit, whereby through the combined operations of the dosage form, the hydromorphone is delivered at a therapeutically effective dose at a rate controlled over a sustained period of time.

Inasmuch as the foregoing specification comprises disclosed embodiments, it is understood what variations and modifications may be made herein, in accordance with the principles disclosed, without departing from the invention.

We claim:

1. A therapeutic composition for the relief of pain comprising 1 to 1000 mg of hydromorphone, 25 to 500 mg of a carboxymethylcellulose possessing a 10,000 to 300,000 molecular weight, 1 to 50 mg of a poly(vinylpyrrolidone) having a 10,000 to 300,000 molecular weight and 0 to 7.5 mg of a lubricant, which therapeutic composition is encased with a semipermeable wall with a passageway through the semipermeable composition.

2. A bilayer comprising a hydromorphone composition that comprises 1 to 1000 mg of hydromorphone. 25 to 500 mg of a carboxymethylcellulose possessing a 10,000 to 300,000 molecular weight, 1 to 50 mg of a poly (vinylpyrrolidone) having, a 10,000 to 300,000 molecular weight, and 0 to 7.5 mg of a lubricant; and an push composition comprising 15 to 250 mg of a poly(alkylene oxide) of 3,000,000 to 7,500,000 molecular weight, 0 to 75 mg of an osmagent, 1 to 50 mg of a hydroxyalkylcellulose, 0 to 10 mg of a tableting lubricant, 0 to 10 mg of an antioxidant, and 0 to 10 mg of a colorant.

3. A method for administering hydromorphone, to a patient in need of pain relief which method comprises admitting orally into the patient a composition comprising 1 to 1000 mg of hydromorphone, 25 to 500 mg of a poly(alkylene oxide) possessing a 150,000 to 500,000 molecular weight, 1 to 50 mg of poly(vinyl pyrrolidone) possessing a 10,000 to 300,000 molecular weight, and 0 to 7.5 mg of a lubricant, an push composition comprising a carboxymethylcellulose having a 450,000 to 2,500,000 molecular weight, and wherein the method administers the hydromorphone at a sustained rate over time for the relief of pain.

4. The method for administering the hydromorphone according to claim 3, wherein the hydromorphone composition and the push composition are surrounded by a semipermeable wall permeable to aqueous biological fluid. and impermeable to the passage of hydromorphone, with a passageway in the semipermeable wall, the poly(alkylene) is replaced by carboxymethylcellulose possessing a 10,000 to 300,000 molecular weight for administering the hydromorphone to the patient for the relief of pain.

* * * * *

UNITED STATES PATENT AND TRADEMARK OFFICE
CERTIFICATE OF CORRECTION

PATENT NO. : 5,529,787

DATED : June 25, 1996

INVENTOR(S) : Sonya Merrill, Atul D. Ayer, Navjot Chadha, Anthony L. Kuczynski

It is certified that error appears in the above-identified patent and that said Letters Patent is hereby corrected as shown below:

Column 8, line 21, before "push composition", "an" should read --a--.

Signed and Sealed this

Twenty-fourth Day of December, 1996

Attest:

BRUCE LEHMAN

Attesting Officer     Commissioner of Patents and Trademarks